United States Patent
Clinton

(10) Patent No.: US 6,892,733 B2
(45) Date of Patent: May 17, 2005

(54) I.V. SLEEVE

(76) Inventor: Dessa O. Clinton, 200 Peale Ct., Cibolo, TX (US) 78108

(*) Notice: Subject to any disclaimer, the term of this patent is extended or adjusted under 35 U.S.C. 154(b) by 0 days.

(21) Appl. No.: 09/988,481

(22) Filed: Nov. 19, 2001

(65) Prior Publication Data

US 2003/0094179 A1 May 22, 2003

(51) Int. Cl.[7] ................................................. A61F 5/37
(52) U.S. Cl. ............................ 128/878; 128/888; 602/3
(58) Field of Search ............................... 128/842, 844, 128/846, 878, 879, 888, 889, 877, 882, DIG. 26; 602/3; 604/179

(56) References Cited

U.S. PATENT DOCUMENTS

| | | | |
|---|---|---|---|
| 2,704,069 A | | 3/1955 | Donelan |
| 3,416,518 A | | 12/1968 | Samuels |
| 3,747,374 A | * | 7/1973 | Meyer ........................ 66/195 |
| 4,016,027 A | | 4/1977 | Kintanar |
| 4,133,624 A | | 1/1979 | Heavner et al. |
| 4,287,608 A | | 9/1981 | Meyer |
| 4,315,504 A | | 2/1982 | Drennan |
| 4,470,410 A | * | 9/1984 | Elliott ................. 128/DIG. 26 |
| 4,646,727 A | | 3/1987 | Chambers |
| 4,856,112 A | | 8/1989 | Effle |
| 4,926,851 A | | 5/1990 | Bulley |
| 4,971,233 A | | 11/1990 | Keenan |
| 4,991,593 A | | 2/1991 | LeVahn |
| 5,016,648 A | | 5/1991 | Brown |
| 5,063,919 A | | 11/1991 | Silverberg |
| 5,143,762 A | | 9/1992 | Ho |
| 5,187,813 A | | 2/1993 | Klein |
| 5,228,851 A | | 7/1993 | Burton |
| 2,169,203 A | | 9/1993 | Hinchliff |
| 5,344,406 A | * | 9/1994 | Spooner ........................ 602/3 |
| 5,357,633 A | | 10/1994 | Rael |
| 5,592,953 A | * | 1/1997 | Delao ............................ 602/3 |

* cited by examiner

Primary Examiner—Michael Brown

(57) ABSTRACT

The nature of the invention is to thoroughly compress the entire length and circumference of a medical site, limb, torso, neck, arm and leg with a tubular elastic sleeve that has openings at both ends. The I.V. Sleeve has bands of compressed elastic reinforcement about its circumference and equidistant throughout its entire length. The purposes of the bands are to reinforce the I.V. Sleeve and protect the compressed integrity of the remainder of the site and sleeve in the event of puncture or rupture of the sleeve in another section. For distribution and packaging it is rolled upon itself like an elastic ring. During use the entire elastic ring is stretched over any obstruction and onto the medical site where it is then unrolled onto the site becoming a skin tight protective barrier. The I.V. sleeve allows for its material to be manufactured with both impregnable and pregnable materials, man made and natural.

7 Claims, 2 Drawing Sheets

I.V. SLEEVE

CROSS REFERENCE TO RELATED APPLICATIONS

U.S. Pat. Documents

| | | | |
|---|---|---|---|
| 3416518 | Dec., 1968 | Samuels | 602/3. |
| 5143762 | Sep., 1992 | Ho | 128/846. |
| 5228851 | Jul., 1993 | Burton | 604/171. |
| 5592953 | Jan., 1997 | Delao | 602/3. |
| 2169203 | Aug., 1939 | Hinchliff | 66/178. |
| 2704069 | Mar., 1955 | Donelan | 128/881. |
| 4016027 | Apr., 1977 | Kintanar | 2/159. |
| 4133624 | Jan., 1979 | Heavner et al. | 425/275. |
| 4287608 | Sep., 1981 | Meyer | 2/16. |
| 4315504 | Feb., 1982 | Drennan | 128/881. |
| 4646727 | Mar., 1987 | Chambers | 128/882. |
| 4856112 | Aug., 1989 | Effle | 2/59. |
| 4926851 | May., 1990 | Bulley | 128/157. |
| 4971233 | Nov., 1990 | Keenan | 223/111. |
| 4991593 | Feb., 1991 | LeVahn | 128/856. |
| 5016648 | May., 1991 | Brown | 128/879. |
| 5063919 | Nov., 1991 | Silverberg | 602/3. |
| 5187813 | Feb., 1993 | Klein | 2/16. |
| 5357633 | Oct., 1994 | Rael | 2/16. |

BACKGROUND OF THE INVENTION

1. Field of Invention

The invention relates to a open ended elasticized device, tubular in shape, designed to compress, encompass, protect, retain, site and or deliver medication to an extremity or thorax of a human or animal.

2. Description of Prior Art

There have been many previous devices for the protection of extremities, appendages or thorax for humans or animals in protecting articles and site from contamination or for preventing water, dirt or hazardous articles from contaminating the site. The suggestion of a single closed-ended bag, glove like device and open-ended tubular device with sealable or elasticized ends presently exists with all of the following U.S. Pat. Nos. 5,357,633, 5,187,813, 5,063,919, 5,016,648, 4,991,593, 4,971,233, 4,926,851, 4,856,112, 4,646,727, 4,315,504, 4,287,608, 4,133,624, 4,016,027, 2,704,069, 2,169,203, 5,592,953, 5,228,851, 5,143,762, 3,416,518. Each of the prior art products although being able to protect extremities from contamination are flawed and limited in their design. The various prior art configurations do nothing to fully compress the site. Compression of the medical site is required to facilitate holding an Intra Venous item, compressing the wound in the event of bleeding, delivery of medication via impregnation to the I.V. Sleeve itself. Compression throughout the entire extremity, thorax and site is as well required in the event of product failure. On all prior art, failure of an elasticized end or puncture to the product would render such product inoperable and useless. The I.V. Sleeve is designed to maintain its integrity even in the event of a tear or puncture.

In addition the I.V. Sleeve is designed to facilitate the manufacturing and field use process by using a simple pre-existing and time proven manufacturing process that not only pre packages and protects the I.V. Sleeve from contamination, but allows it to be carried in to the field in a disposable pack like that of a Handy-Wipe or condom.

Prior art product have as well failed to maintain pace with modern medicine. All prior art fails to deliver medication to the site. The I.V. Sleeves ability to fit skin tight and its ability to be manufactured using a vast number or different materials allows it to be impregnated with medication so that such medication can be delivered through skin absorption. Unlike prior art product the I.V. Sleeve's ability to be manufactured from skin type products allows for exceptional seamless coverage and medication in the event of skin grafts required for large areas.

BRIEF SUMMARY OF THE INVENTION

The object of the invention is to have field usable cost effective product that can fully protect an extremity, appendage and thorax during pre and post medical procedures. The I.V. Sleeve is used for humans and animals. It compresses the entire wound or medical site to maintain the integrity of the procedure and to deliver medication when desired.

The I.V. Sleeve is manufactured with materials that fit the environmental parameters dictated by the wound or medical procedure in itself. In the event of grafts, the I.V. Sleeve is manufactured from skin. It can be waterproof yet breathable and maintains it's anti contaminant integrity even in the event of puncture or tear. Its elasticity allows for ability to protect a human thorax as well as a leg, arm or finger.

DETAILED DESCRIPTION OF INVENTION

Figure 1:
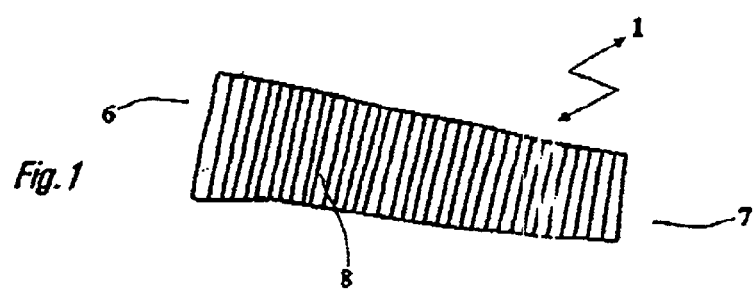
FIG. 1 is an elasticized tub with openings at both ends.
Figure 2:
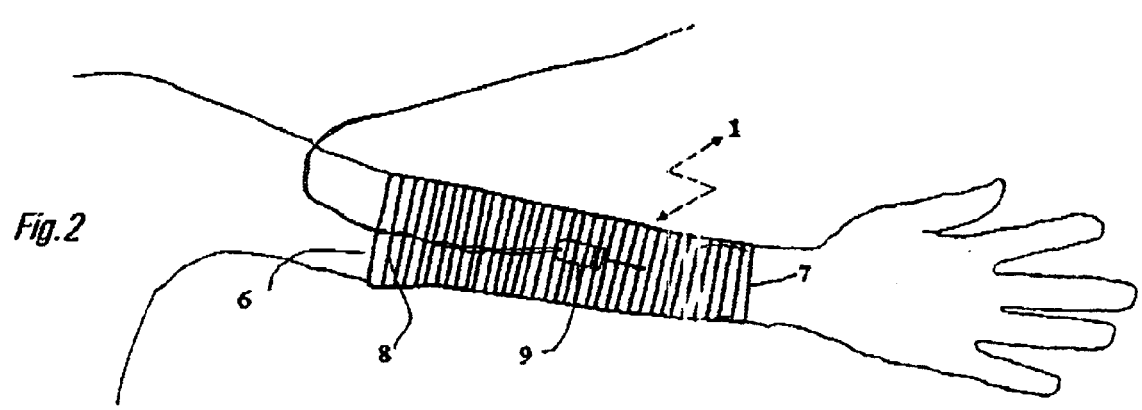

The invention relates to a skintight elastic sleeve that is reinforced with elastic bands 8 throughout its entire circumference and length as seen in FIG. 1. To be fitted onto appendages, extremities, neck or thorax for achieving complete site compression, protection, and for maintenance of integrity of a medical site or intravenous equipment 9. Whereas the sleeve body 1 and band 8 are manufactured from a group of elastic, pliable and expendable materials singularly and in combination such as rubber, latex, silicone, Gore-Tex, epidermal tissue, smooth muscle tissue, plastic and plastic components that are capable of expanding to 3 times its original state.

Figure 3:
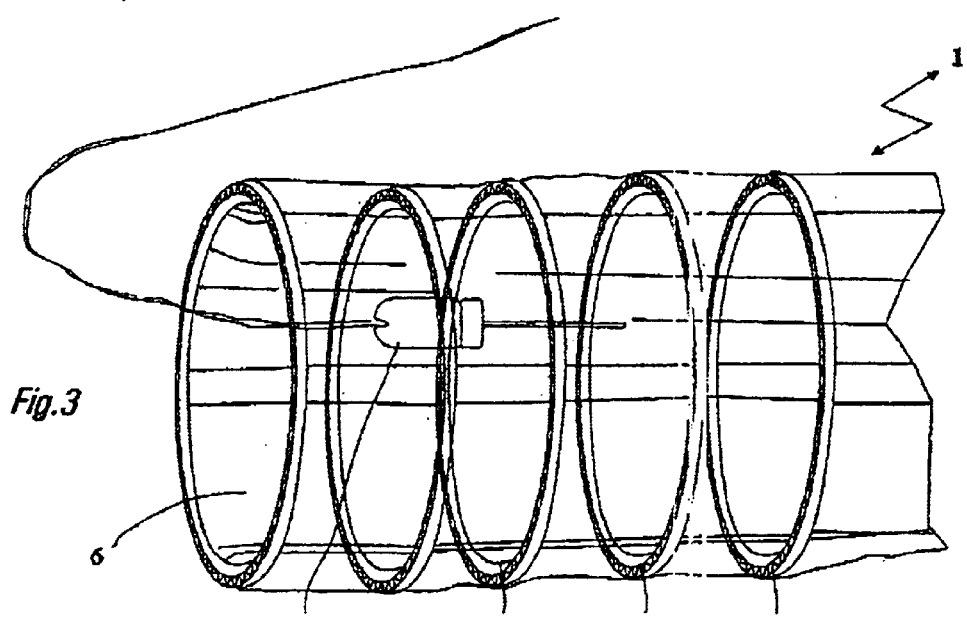
Figure 4:
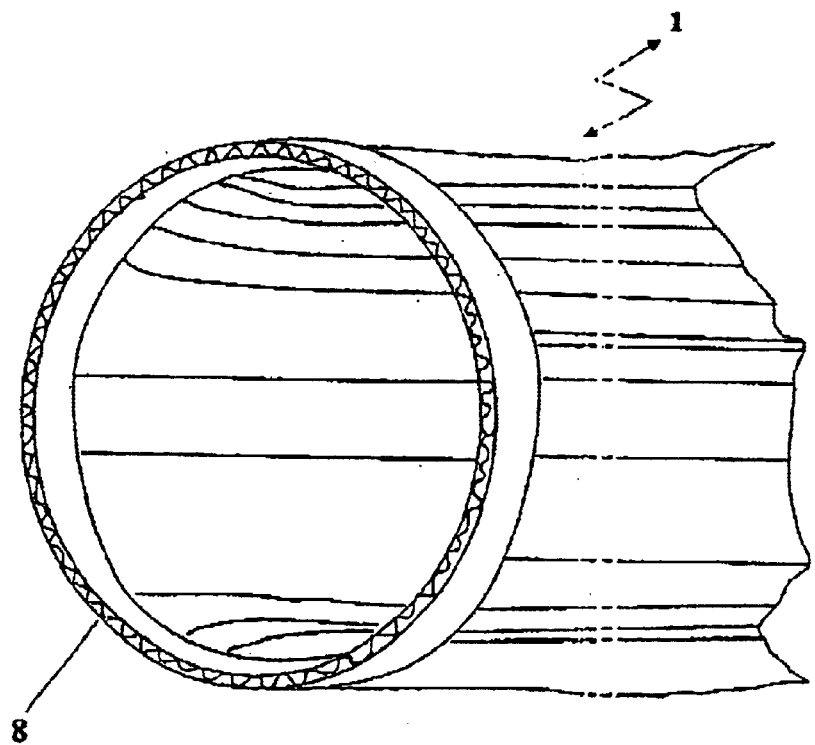
Figure 5:
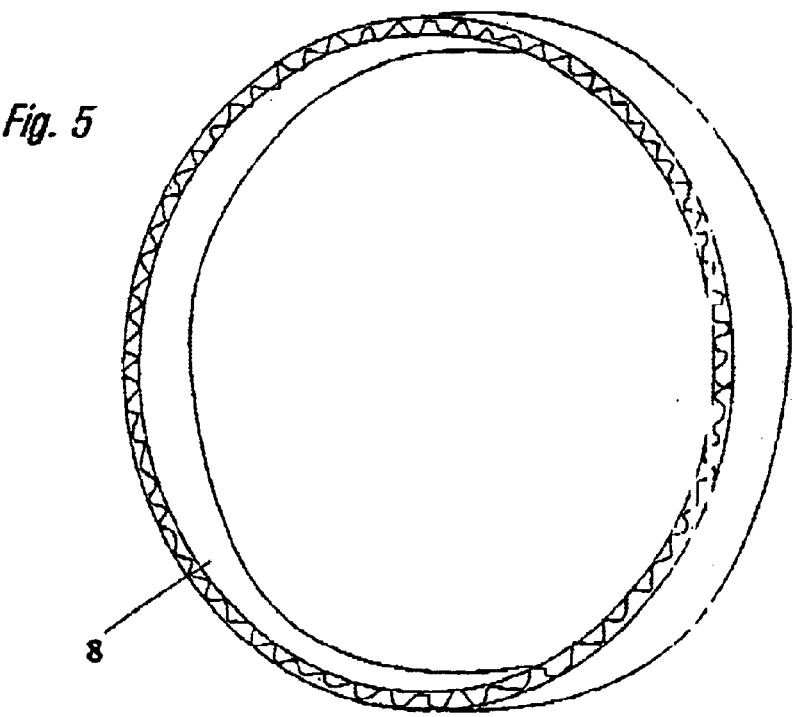

The sleeve is cylindrical in shape with openings at both ends 6 and 7. The body or the sleeve 1 shall be of sufficient thickness to protect the medical site while maintaining sufficient transparency to view such site without the need to remove the sleeve. The bands 8 around the sleeve shall be of identical material used in the manufacturing of the body 1 of the sleeve so to facilitate the manufacturing process. The body 1 of the sleeve and band 8 are of identical diameter and elasticity so as to apply sufficient force for sealing the sleeve end 6 and 7 without inhibiting circulation. Multiple bands 8 are fitted throughout the circumference and entire length of sleeve separated by a distance of 2.54 cm or 1 inch from each other as seen in FIG. 3. As an example: If the length of the sleeve was 25.40 cm or 10 inches then there would be a total of 11 bands. First band 8 would initiate at end 6. The second band would be 2.54 cm or 1 inch from the first and each consecutive band would be 2.54 cm from the previous until the final and eleventh band terminated on end 7. If the length of the sleeve was 20 inches then there would be twice as many bands 8. The bands 8 between the ends 6 and 7 are manufactured by collecting 2 cm of body 1 material around the entire circumference of the sleeve and then folding and adhering the material back onto the body 1 as shown in FIG. 6B, C. The band 8 prohibits the sleeve from loosing its integrity if punctured or damaged. The elastic body 1 will no longer be able to tear and destroy the integrity of the entire sleeve and site. In storage the sleeve is outwardly rolled upon itself to form a lightweight elastic ring. Method of installation is that of first securing medical site with intravenous medical procedures, cleaning, medications etc. Then stretching the elastic ring over extremity and onto the site to be protected. You then unroll the I. V. sleeve out from itself and onto and over the medical site. This finalizes the installation process.

What is claimed is:

1. A protective sleeve comprising a tubular member having first and second ends, a longitudinal axis and open on both ends, said tubular member being made of an elastic material, a plurality of bands extending along the longitudinal axis of said tubular member, said bands being 1 mm to 2 mm in thickness and spaced apart an equal distance of 2.5 cm along the longitudinal axis, said tubular member being 2.5 cm to 80 cm in diameter.

2. The protective sleeve of claim 1, wherein the elastic material is latex.

3. The protective sleeve of claim 1, wherein the elastic material is silicone.

4. The elastic sleeve of claim 1, wherein the elastic material is plastic.

5. The elastic sleeve of claim 1, wherein the elastic material is breathable.

6. The protective sleeve of claim 1, wherein the sleeve is adapted to be rolled into the configuration of a rolled condom.

7. The protective sleeve of claim 1, wherein the sleeve is made of a material is made of a thickness that allows transparency for visual verification and maintenance of any medical site under the sleeve.

* * * * *